United States Patent [19]

Guyer et al.

[11] Patent Number: 4,631,305

[45] Date of Patent: Dec. 23, 1986

[54] POLYMERIC MATERIAL AS A DISINTEGRANT IN A COMPRESSED TABLET

[75] Inventors: Thomas L. Guyer, Richland; Robert M. Franz, Otsego, both of Mich.

[73] Assignee: The Upjohn Company, Kalamazoo, Mich.

[21] Appl. No.: 714,786

[22] Filed: Mar. 22, 1985

[51] Int. Cl.$^4$ .................... A61K 9/20; A61K 47/00; C08L 63/00; C08L 25/04

[52] U.S. Cl. .................... 523/400; 424/14; 424/78; 514/772; 514/789; 514/960; 524/555; 524/578

[58] Field of Search .................... 424/22, 32, 78, 14; 514/789, 960, 772; 523/400; 524/555, 578

[56] References Cited

U.S. PATENT DOCUMENTS

| | | | |
|---|---|---|---|
| 2,591,573 | 4/1952 | McBurney | 521/32 |
| 2,644,760 | 7/1953 | Schroeder | 106/28 |
| 3,002,823 | 10/1961 | Flodin et al. | 23/293 |
| 3,152,188 | 10/1984 | Kirkpatrick et al. | 564/506 |
| 3,308,020 | 3/1967 | Wolf | 167/65 |
| 3,308,217 | 3/1967 | Lowy et al. | 514/961 |
| 3,332,841 | 7/1967 | Ainsworth et al. | 167/55 |
| 3,383,281 | 4/1968 | Wolf et al. | 167/65 |
| 3,692,895 | 9/1972 | Nelson | 424/78 |
| 3,803,237 | 4/1974 | Lednicer et al. | 528/409 |
| 4,007,258 | 2/1977 | Cohen et al. | 514/965 |
| 4,221,778 | 9/1980 | Raghunsthan | 424/31 |
| 4,353,887 | 10/1982 | Hess et al. | 424/14 |
| 4,439,419 | 3/1984 | Strack | 423/329 |
| 4,539,198 | 9/1985 | Powell et al. | 514/960 |

OTHER PUBLICATIONS

Martindale, The Extra Pharmacopoeia, 28th Edition, edited by Reynolds, published by The Pharmaceutical Press, London, Dec., 1982.

D. Gissinger and A. Stamm, "A Comparative Evaluation of the Properties of Some Tablet Disintegrants", Drug. Develop. Ind. Pharm., 6, 511 (1980).

E. M. Rudnic et al., "Some Effects of Relatively Low Levels of Eight Tablet Disintegrants on a Direct Compression System", Drug. Develop. Ind. Pharm., 7, 347-358 (1981).

H. A. Lieberman et al., Pharmaceutical Dosage Forms: Tablets, vol. 1, pp. 139-140.

R. E. Gordon, "The Thermodynamic Characterization of the Solid Surface Interaction for Three Tablet Disintegrating Agents", Ph.D. Thesis, Purdue, (1981), Dissertation Abstracts.

Jones, et al., "The Polymerization of Ethylenimine", J. Org. Chem., 9:125-147 (1944).

E. H. Gause et al., "Purification of Tetraethylenepentamine", Amer. Chem. Soc., 73:5457 (Nov.) 1951.

W. M. Hutchinson et al., "Prolysis of Some Polyethlene Amines", J. Amer. Chem. Soc., 67:1966 (Nov.) 1945.

Ionescu et al., Chem. Abstracts, 64:1357 (1966).

Peterson et al., J. Am. Chem. Soc., 78:751-755 (1956).

McKernan & Ricketts, Chemistry and Industry, Nov. 21, 1959, pp. 1490-1491.

Primary Examiner—Ronald W. Griffin
Attorney, Agent, or Firm—William G. Jameson

[57] ABSTRACT

Compressed tablets containing polymeric material as a disintegrant. A particular material is colestipol hydrochloride.

12 Claims, No Drawings

POLYMERIC MATERIAL AS A DISINTEGRANT IN A COMPRESSED TABLET

DESCRIPTION

1. Brief Description of the Invention

This invention relates to the new use of known polymeric materials as a tablet disintegrating agent in compressed tablets. The polymeric material is selected from the group consisting of (1) a copolymer of a polyethylenepolyamine and a bifunctional substance, as the free base or partial acid addition salt form thereof, one such polymeric material being known by the name colestipol hydrochloride;

(2) a copolymer of polystyrene cross-linked with up to about 5% w/w divinylbenzene and containing quaternary ammonium groups, one such polymeric material being known as cholestyramine;

(3) a polyethylene imine polymer cross-linked by reaction with a polyfunctional halogen compound;

(4) a polyalkyleneimine polymer prepared by cross-linking a polyalkyleneimine with linking groups containing from about 2 to 10 carbon atoms, and having a molecular weight of about 20 to about 200.

2. Background of the Invention

Of the multitude of forms in which pharmaceutical products may be dispensed, the compressed tablet form is, by far, that most frequently employed today. The compressed tablet provides definite practical advantages over liquid and powder preparations. For this reason, practically every medicament capable of being embodied in such tablet has been marketed in this form. Convenience to patient, physician and pharmacist, ease of administration and, most important, accuracy of dosage are among the advantages that have led to the constantly increasing use of medicament-containing compressed tablets. Furthermore, the development of machinery for the high speed, large volume production of uniform tablets has been responsible for their steadily growing importance in the pharmaceutical trade.

In fields other than the pharmaceutical, the compressed tablet also plays an important role as a dispensing unit of a wide variety of materials. Perhaps most familiar are the tableted laundry products, such as detergents and bleaches, that are sold today in competition to powdered or liquid products. Nevertheless, such diverse materials as perfumed bath water softeners, confections, artificial sweeteners, plant foods, weed killers and dyes are widely marketed as compressed tablet formulations.

In addition to the active or therapeutic ingredient, tablets contain a number of inert materials. The latter are known as additives or "adds". They may be classified according to the part they play in the finished tablet. The first group contains those which help to impart satisfactory compression characteristics to the formulation. These include (1) diluents, (2) binders, and (3) lubricants. The second group of added substances helps to give additional desirable physical characteristics to the finished tablet. Included in this group are (1) disintegrants, (2) colors, and in the case of chewable tablets, (3) flavors, and (4) sweetening agents.

A disintegrant is a substance, or a mixture of substances, added to a tablet to facilitate its breakup or disintegration after administration. The active ingredient must be released from the tablet matrix as efficiently as possible to allow for its rapid dissolution. Materials serving as disintegrants have been chemically classified as starches, clays, celluloses, algins, or gums.

The most popular disintegrants are corn and potato starch which have been well-dried and powdered. Starch has a great affinity for water and swells when moistened, thus facilitating the rupture of the tablet matrix. However, others have suggested that its disintegrating action in tablets is due to capillary action rather than swelling; the spherical shape of the starch grains increases the porosity of the tablet, thus promoting capillary action. When their disintegration effect is desired, starches are added to the powder blends in the dry state. Starch pastes which are useful as binding agents will generally not be effective as disintegrating agents.

In addition to the starches a large variety of materials have been used and are reported to be effective as disintegrants. This group includes Veegum HV, Ac-Di-Sol, methylcellulose, agar, bentonite, cellulose and wood products, natural sponge, cation-exchange resins (e.g., Amberlite IRP-88), alginic acid, guar gum, citrus pulp, and carboxymethylcellulose.

See for example: D. Gissinger and A. Stamm. Drug Develop. Ind. Pharm., 6, 511 (1980), "A Comparative Evaluation of the Properties of Some Tablet Disintegrants"; E. M. Rudnic, C. T. Rhodes, J. F. Bavitz, and J. B. Schwartz, Drug Develop. Ind. Pharm., 7, 347 (1981), "Some Effects of Relatively Low Levels of Eight Tablet Disintegrants on a Direct Compression System"; H. A. Lieberman and L. Lachman, Pharmaceutical Dosage Forms: Tablets, Volume 1, pages 139–140; and R. E. Gordon, The Thermodynamic Characterization of the Solid Surface Interaction for Three Tablet Disintegrating Agents, Ph.D. Thesis, Purdue University, 1981.

The use of resins in prolonged release pharmaceutical preparations is disclosed in U.S. Pat. No. 4,221,778.

Sodium lauryl sulfate in combination with starch also has been demonstrated to be an effective disintegrant. In some cases the apparent effectiveness of surfactants in improving tablet disintegration is postulated as being due to an increase in the rate of wetting.

The polymeric material used as a disintegrant in the tablet of the present invention is a known material and has been previously used medicinally as a cholesterol lowering agent. The material has been administered to humans in powder form or suspended in water or other suitable liquid carrier.

DETAILED DESCRIPTION

In accordance with the manner and process of using the present invention, a sufficient amount of the polymeric material to initiate disintegration is incorporated in the tablet mixture before it is compressed into tablets.

The polymeric materials utilized in the present invention are described hereafter.

The polyethylenepolyamines used in preparing the copolymers are those of the ethylenediamine series containing from 2 to about 10 ethylene units, the molecular weight ranging from about 103 to an average molecular weight of about 450. A lower member of the series, diethylenetriamine, molecular weight about 103, is usually available commercially in both pure and commercial grades. Triethylenetetramine, tetraethylenepentamine, pentaethylenehexamine, and the higher homologs are usually available as commercial grades containing aliphatic and also some cyclic polyethylenepolyamines. See, for example, the disclosure of mixed residues containing up to about 10 alkylene groups in U.S. Pat. No. 3,152,188. Commercially available polyethylenepolyamines are derived, for example, from the reaction of ethylene dichloride and ammonia or the controlled polymerization of ethyleneimine. Jones, et al, J. Org. Chem. 9:125-147 (1944) describe the polymerization of ethyleneimine by catalysts such as acids, boron trifluoride and ammonia. Polyethylenepolyamines therein described include diethylenetriamine, triethylenetetramine, tetraethylenepentamine, heptaethyleneoctamine, nonaethylenedecamine, as well as higher molecular weight polymers with lesser amounts of amino nitrogen. Gause, et al, J. Amer. Chem. Soc. 73:5457 (Nov) 1951 describe purification of tetraethylenepentamine on an ion exchange column. Hutchinson, et a., J. Amer. Chem. Soc. 67:1966 (Nov) 1945 describe formation of diethylenetriamine, triethylenetetramine, tetraethylenepentamine and similar compounds of higher molecular weights, the latter being found in an "amine residue" after removal of the lower members by distillation. Ionescu and Anghelescu, Chem. Abstracts 64:1357 (1966) describe gas chromatographic analysis of polyethylenepolyamines which indicates that ethylenediamine, diethylenetriamine, triethylenetetramine, tetraethylenepentamine and pentaethylenehexamine are usually present in mixtures. Polyalkylenepolyamines are usually present in mixtures. Polyalkylenepolyamines are also described and used in U.S. Pat. Nos. 2,644,760 and 3,152,188. Those described in U.S. Pat. No. 2,644,760 are polyamines of the ethylenediamine series and include, for example, tetraethylenepentamine, triethylenetetramine, diethylenetriamine, pentaethylenehexamine, and the like. Those described in U.S. Pat. No. 3,152,188 include diethylenetriamine, triethylenetetramine and tetraethylenepentamine in pure form or as mixtures, and higher polyalkylenepolyamine homologs which are usually marketed as mixed residues containing up to approximately 10 alkylene units.

Polyethyleneimine polymers are described and used in U.S. Pat. Nos. 3,308,020 and 3,332,841. Those in the former have an average molecular weight of about 30,000 and those in U.S. Pat. No. 3,332,841 have an average molecular weight of from about 800 to about 100,000. However, in the present invention, a molecular weight range of from about 103 (diethylenetriamine) to an average molecular weight of about 450 includes those polyethylenepolyamines useful for the preparation of cross-linked copolymers adminstered orally. The aforesaid polyethylenepolyamines are available as marketed products of variouss suppliers such as Dow Chemical Company, Industrial Chemical & Dye Company, Union Carbide, Aldrich Chemical Co., and Eastman Kodak. Typically supplied commercial tetraethylenepentamine (Union Carbide) has nominal values as follows: apparent specific gravity, 20/20° C., 0.9980; boiling point 760 mm., 340° C. (decomposes); completely soluble in water; flash point, ASTM method D92, Cleveland Open Cup, 365° F.

In order to prepared the copolymers for the inventive process, such polyethylenepolyamines are copolymerized and cross-linked with bifunctional compounds having epoxy groups and/or halogen atoms; for example, epichlorohydrin, glycerol-1,3-dichlorohydrin, 1,2:3,4-diepoxybutane, bis-epoxypropyl ether, ethylene glycol bis-epoxypropyl ether and 1,4-butanediol bis-epoxypropyl ether according to known methods; for example, those of British Pat. No. 628,821; U.S. Pat. No. b 3,002,823; Peterson and Sober, J. Am. Chem. Soc. 78:751-755 (1956), and McKernan and Ricketts, Chemistry and Industry, Nov. 21, (1959), pgs. 1490-1491. Illustratively, with epichlorohydrin as cross-linking agent the copolymer contains cross-links represented by $-CH_2CH(OH)CH_2-$; with 1,2:3,4-diepoxybutane by $-CH_2CH(OH)CH(OH)CH_2-$; with bis-epoxypropyl ether by $-CH_2CH(OH)CH_2OCH_2CH(OH)CH_2-$. Similarly, with ethylene glycol bis-epoxypropyl ether the copolymer contains cross-links represented by $-CH_2CH(OH)CH_2OCH_2CH_2OCH_2CH(OH)CH_2-$, and in the case of 1,4-butanediol bis-epoxypropyl ether by $-CH_2CH(OH)CH_2O(CH_2)_4OCH_2CH(OH)CH_2-$. Hence, these copolymer cross-linked products contain a residue of an aliphatic radical having three to ten carbon atoms inclusive. The content of cross-linking moiety expressed as percent (%) by weight of the copolymer is at least 10%, preferably at least 14%, and reaches in some cases 47% or higher. Both the partial acid addition salts and free base forms of the cross-linked copolymer are operable in the present compositions and processes. Illustratively, a pharmaceutically acceptable hydrochloric acid addition salt form is prepared by controlling the amounts of the polyethylenepolyamine and bifunctional reactant and using calculated amounts of base, e.g., sodium hydroxide, in adjusting the reaction mixture, for example 20 moles of tetraethylenepentamine, 50 moles of epichlorohydrin and 50 moles of sodium hydroxide provide a cross-linked copolymer in the form of a partial hydrochloride. Alternately, an acid addition salt is prepared from an aqueous solution, dispersion or susspension of a free base copolymer by adjustment with the desired acid, such as phosphoric, citric, sulfuric, hydrochloric and the like. For example, 650 gm of free base copolymer of tetraethylenepentamine and epichlorohydrin and 75 gm of sulfuric acid provide a copolymer partial sulfate. Illustratively, free base forms are usually prepred by adding excess alkali, e.g., sodium hydroxide, to the reaction mixture of a particular amine and bifunctional reactant, thus obtaining an alkaline aqueous dispersion or suspension of the free base. Washing with distilled or deionized water until the washings are free of the acid ion and free of alkali provides the base which is dried at about 80° C. and milled to a uniform granular solid.

Colestipol hydrochloride is a high molecular weight, highly crosslinked, basic anion-exchange copolymer formed by the reaction of one molar equivalent of diethylenetriamine with 1.8-2.0 molar equivalents of epichlorohydrin, with approximately one of five amine nitrogens protonated (chloride form). See U.S. Pat. Nos. 3,692,892 and 4,439,419.

A preferred method for preparing the polymer for medical use is disclosed in U.S. Pat. No. 3,803,237, issued Apr. 9, 1974, and is known as the "bead process".

A copolymer of polystyrene cross-linked with up to about 5% w/w divinylbenzene and containing quaternary ammonium groups is defined as a polystyrene-divinylbenzene polymer as described in U.S. Pat. Nos. 3,383,281 and 2,591,573. Therein described is a class of resins which are known as "Dowex 1" resins and which are polystyrene resins crosslinked with varying percentages (up to about 5%) of divinylbenzene and which are manufactured by Dow Chemical Company, Midland, Mich. Quarternary ammonium groups are introduced into such resins by chloromethylation of the aromatic rings and replacement of the chlorine by a tertiary amine such as trimethylamine to form, e.g., a trimethylammonium group.

The above polymers can be further modified by using any other tertiary amine, e.g., dimethylamine ethanol, pyridine, picoline, etc. The extent of chloromethylation can be varied so that the number of active quaternary ammonium groups per chain is varied. The aromatic ring can have other substituents such as chlorine or methyl. These resulting quaternary ammonium containing polystyrene-divinylbenzene cross-linked copolymers and their nontoxic salts including chloride, sulfate, acetate, phosphate, and the like or as the hydroxyl form are useful in the present compositions.

A polyethylene imine polymer cross-linked by reaction with a polyfunctional halogen compound is defined as a cross-linked polyethylene imine polymer as described in U.S. Pat. No. 3,383,281 and comprising the polyethylene imines which have been cross-linked by reaction with a polyfunctional halogen compound, the halogen being displaced by the imine nitrogens in the chain with loss of the hydrogen, and the amount of cross-linking being kept to a minimum.

A polyalkyleneimine polymer prepared by cross-linking a polyalkyleneimine with linking groups containing from about 2 to 10 carbon atoms, and having a molecular weight of about 20 to about 200 is defined as polymer so obtained as described in U.S. Pat. No. 3,332,841. Therein are described water-insoluble, solid, cross-linked polyalkyleneimine polymers, wherein the alkylene moiety preferably contains 2 to 4 carbon atoms, said polyalkleneimine polymer being prepared by cross-linking a polyalkyleneimine with linking groups containing from about 2 to 10 carbon atoms, and having a molcular weight of about 20 to about 200.

For most purposes, and particularly for pharmaceutical applications, a hard non-friable tablet possessing acceptable disintegration and dissolution characteristics is the goal of the tablet manufacturer.

The tablets can be prepared using conventional methods and machinery. In general the ingredients in power form are mixed together and fed into a tableting machine. Intermediate steps after mixing the powders can be for example wet or dry granulation, slugging or direct compression.

The polymeric material comprises from about 0.4% w/w to about 10% w/w, preferably about 0.5% w/w to about 5% w/w, of the finished tablet. Disintegration times are proportional to the particle size of the polymer, i.e., the smaller the size of the particle the faster the disintegration time. The disintegration and dissolution times are proportional to the polymer concentration, i.e., the greater the polymer concentration, the faster the disintegration/dissolution time.

Advantageously, the disintegration/dissolution times are independent of compressional force.

EXAMPLE 1

The following basic formulation was used in this study.

| Ingredient | Amt/tab (mg) |
|---|---|
| Tolbutamide USP Milled | 500 |
| Dibasic Calcium Phosphate USP Anhydrous, 325 mesh | 25 |
| Dried Aluminum Hydroxide Gel USP | 10 |
| Magnesium Stearate USP Powder Food Grade | 2.25 |

Colestipol HCl was added to the above formulation in amounts of 0.04%, 0.4%, 1.0%, and 4% w/w in particle sizes between 100 and 200 mesh (74 to 149$\mu$ (microns)) (United States Standard Sieve Series) and in amounts of 0.5%, 1.0% and 2% w/w in particle size less than 200 mesh (74$\mu$). Tablets were made containing 0% Colestipol that were used as a control in order to judge the effect of this disintegrant.

The tablets were produced in the following manner. One-half of the tolbutamide, the dibasic calcium phosphate, dried aluminum hydroxide gel and Colestipol Hydrochloride were screened through a #20 screen into an 8 quart P-K blender. The remainder of the tolbutamide was then mixed for 10 min. A portion of the mix was removed, combined with the magnesium stearate, and passed through a #20 screen into the P-K blender. The total powder blend was then mixed for an additional 5 min. The samples were compressed at 2400 pounds compressional force. Punches and dies were 15/32" production type tooling. No processing problems (i.e., flow) were encountered during production. Additional samples containing 2% Colestipol hydrochloride (<200 mesh, i.e., <74$\mu$) were compressed at 3000 to 3400 pounds.

Dissolution, disintegration, hardness, friability, and thickness tests were performed according to standard-type procedures.

Samples of 100 tablets each were placed on stability at 25° C./45% RH (relative humidity) and 40° C./75% RH for approximately 2 months (61 days). The tablets were packaged in HDPE (high density polyethylene) plastic bottl4es with plastic caps. The bottles contained no fillers. The above mentioned tests (except thickness) were performed periodically.

The results of disintegration tests are recorded in Table I and dissolution in Table II.

TABLE I

| | | | Disintegration After 61 Days | |
|---|---|---|---|---|
| Colestipol HCl Mesh Size | % Colestipol HCl | Disintegration+ | 25° C./ 45% RH | 40° C./ 75% RH |
| 74–149 microns | 0% | >30 min | >30 min | >30 min |
| 74–149 microns | 0.04% | >30 min | >30 min | >30 min |
| 74–149 microns | 0.40% | 61–162 sec | 60–78 sec | >30 min |
| 74–149 microns | 1.00% | 24–29 sec | 26–34 sec | 85–124 sec |
| 74–149 microns | 4.00% | 18–21 sec | 19–21 sec | 20–23 sec |
| <74 microns | 0% | >30 min | >30 min | >30 min |
| <74 microns | 0.5% | 25–32 sec | 30–37 sec | >30 min |
| <74 microns | 1.0% | 18–21 sec | 23–25 sec | 80–150 sec |
| <74 microns | 2.0% | 14–17 sec | 17–21 sec | 25–29 sec |
| <74 microns | 2.0%[1] | 20–22 sec | 15–18 sec | 22–28 sec |
| <74 microns | 2.0%[2] | 18–22 sec | 16–19 sec | 24–27 sec |

[1]Compressional Force = 3000 lbs.
[2]Compressional Force = 3400 lbs.
Note:
All others - Compressional Force - 2400 lbs.
+Initial

TABLE II

| | Time to reach % dissolved (min) | | | | | | | | |
|---|---|---|---|---|---|---|---|---|---|
| % Colestipol HCl | T50% | | | T70% | | | T90% | | |
| | Avg. | Hi | Low | Avg. | Hi | Low | Avg. | Hi | Low |
| 2%[1] | 3.4 | 3.6 | 3.2 | 6.8 | 9.7 | 5.2 | 12.6 | 16.5 | 10.4 |
| 2%[2] | 3.5 | 3.8 | 3.2 | 6.3 | 7.3 | 5.6 | 11.5 | 12.8 | 10.5 |
| 2% | 3.1 | 3.4 | 2.6 | 5.2 | 6.0 | 4.4 | 9.7 | 11.4 | 08.0 |
| 1% | 5.7 | 6.9 | 4.6 | 12.1 | 16.7 | 6.3 | — | — | — |
| 0.5% | 13.5 | 15.4 | 11.4 | 21.7 | 24.0 | 19.0 | — | — | — |

TABLE II-continued

| % Col-estipol HCl | Time to reach % dissolved (min) | | | | | | | | |
|---|---|---|---|---|---|---|---|---|---|
| | T50% | | | T70% | | | T90% | | |
| | Avg. | Hi | Low | Avg. | Hi | Low | Avg. | Hi | Low |
| 0% | 12–15% Dissolved in 57–58 min | | | | | | | | |

[1] Compressional Force = 3400 lbs
[2] Compressional Force = 3000 lbs.
Note:
All others - Compressional Force - 2400 lbs.

We claim:

1. A compressed tablet comprising an effective disintegrating amount of a disintegrant selected from the group consisting of:
   (1) the free base or partial acid addition salt form of a cross-linked copolymerization product of (a) a polyethylenepolyamine containing from about 2 to about 10 ethylene units and (b) a member selected from the group consisting of epichlorohydrin, glycerol-1,3-dichlorohydrin, 1,2:3,4-diepoxybutane, bis-epoxypropyl ether, ethylene glycol bis-epoxypropyl ether and 1,4-butanediol bis-epoxypropyl ether;
   (2) a copolymer of polystyrene cross-linked with up to 5% w/w divinylbenzene and containing quaternary ammonium groups;
   (3) a polyethylene imine polymer cross-linked with a polyfunctional halogen compound; and
   (4) a polyalkyleneimine polymer prepared by cross-linking a polyalkyleneimine with linking groups containing from about 2 to 10 carbon atoms and having a molecular weight of about 20 to about 200.

2. The tablet of claim 1 wherein the amount of the selected member is from about 0.5% w/w to about 5% w/w of the tablet.

3. The tablet of claim 1 wherein the member selected is the free base or partial acid addition salt form of a cross-linked copolymerization product of (a) a polyethylenepolyamine containing from about 2 to about 10 ethylene units and (b) a member selected from the group consisting of epichlorohydrin, glycerol-1,3-dichlorohydrin, 1,2:3,4-diepoxybutane, bis-epoxypropyl ether, ethylene glycol bis-epoxypropyl ether and 1,4-butanediol bis-epoxypropyl ether.

4. The tablet of claim 3 wherein the polyethylenepolyamine is tetraethylenepentamine and the member is epichlorohydrin.

5. The tablet of claim 3 wherein the amount of the member is from about 0.5% w/w to about 5% w/w of the tablet.

6. The tablet of claim 3 wherein the polyethylenepolyamine is diethylenetriamine and the member is epichlorohydrin.

7. The tablet of claim 1 wherein the member selected is a copolymer of polystyrene cross-linked with up to 5% w/w of divinylbenzene and containing quaternary ammonium groups.

8. The table of claim 7 wherein the amount of member is from about 0.5% w/w to about 5.0% w/w of the tablet.

9. The tablet of claim 1 wherein the member selected is a polyethylene imine polymer cross-linked with a polyfunctional halogen compound.

10. The table of claim 9 wherein the amount of member is from about 0.5% w/w to about 5% w/w of the tablet.

11. The tablet of claim 1 wherein the member selected is a polyalkyleneimine polymer prepared by cross-linking a polyalkyleneimine with linking groups containing from about 2 to 10 carbon atoms and having a molecular weight of about 20 to about 200.

12. The tablet of claim 11 wherein the amount of the selected member is from about 0.5% w/w to about 5% w/w of the tablet.

* * * * *